US 6,635,794 B2

(12) United States Patent
Kishimoto

(10) Patent No.: US 6,635,794 B2
(45) Date of Patent: Oct. 21, 2003

(54) CATALYSTS FOR OXIDATIVE DEHYDROGENATION OF ALKANES AND A PROCESS FOR PRODUCING OLEFINS

(75) Inventor: Nobuji Kishimoto, Himeji (JP)

(73) Assignee: Nippon Shokubai Co Ltd, Osaka (JP)

(*) Notice: Subject to any disclaimer, the term of this patent is extended or adjusted under 35 U.S.C. 154(b) by 4 days.

(21) Appl. No.: 09/983,086

(22) Filed: Oct. 23, 2001

(65) Prior Publication Data

US 2002/0077518 A1 Jun. 20, 2002

(30) Foreign Application Priority Data

Oct. 26, 2000 (JP) ........................................ 2000-326943

(51) Int. Cl.[7] ............................................... C07C 5/333
(52) U.S. Cl. .......................... 585/661; 585/658; 585/660
(58) Field of Search .................... 585/658, 660, 585/661

(56) References Cited

U.S. PATENT DOCUMENTS

| 3,316,057 A | | 4/1967 | Howk |
| 4,131,631 A | * | 12/1978 | Hardman |
| 4,370,259 A | * | 1/1983 | Eastman et al. |
| 4,621,163 A | | 11/1986 | Kolts |
| 4,777,319 A | * | 10/1988 | Kung et al. |
| 5,637,545 A | * | 6/1997 | Lewis |

FOREIGN PATENT DOCUMENTS

| CN | 1073893 | * | 10/1992 |
| EP | 0 379 433 | * | 7/1990 |
| EP | 0963788 | | 12/1999 |
| JP | 2000-37624 | * | 2/2000 |
| JP | 2000-37625 | * | 2/2000 |
| WO | WO 93/02776 | | 2/1993 |

OTHER PUBLICATIONS

Neftekhimiya (1990), 30(2) 207–10 and its English abstract.
J. Chem. Commun. (1991) (8) 558–9.
Catal. Lett. (1996), 37, (3,4), 241–6.
ACS Symp. Ser. (1996), 638 (Heterogeneous Hydrocarbon Oxidation) 155–169.
Database WPI, Section Ch. Week 199722, Derwent Publications Ltd., XP002190468 & JP 09 075733, Apr. 25, 1977.
Gerhartz W. and Yamamoto Y.S. (Editors), "Ullmann's Encyclopedia of Industrial Chemistry" Edition 5, vol. A16. p. 124.

* cited by examiner

*Primary Examiner*—Thuan D. Dang
(74) *Attorney, Agent, or Firm*—Sherman & Shalloway

(57) ABSTRACT

Novel oxidative dehydrogenation catalysts which are useful in vapor-phase oxidative dehydrogenation of lower alkanes with molecular oxygen to produce corresponding olefins at high yields are provided. The catalysts are characterized by containing Mn as the essential component and a crystal phase which is identified by the peaks appearing on their X-ray diffraction spectra (per Cu—Kα cathode) where the diffraction angle 2θ (±0.3°) is at 32.9°, 55.2°, 23.1°, 38.2° and 65.8°. The use of those catalysts enables production of the olefins at high yields.

2 Claims, 4 Drawing Sheets

Figure 1:
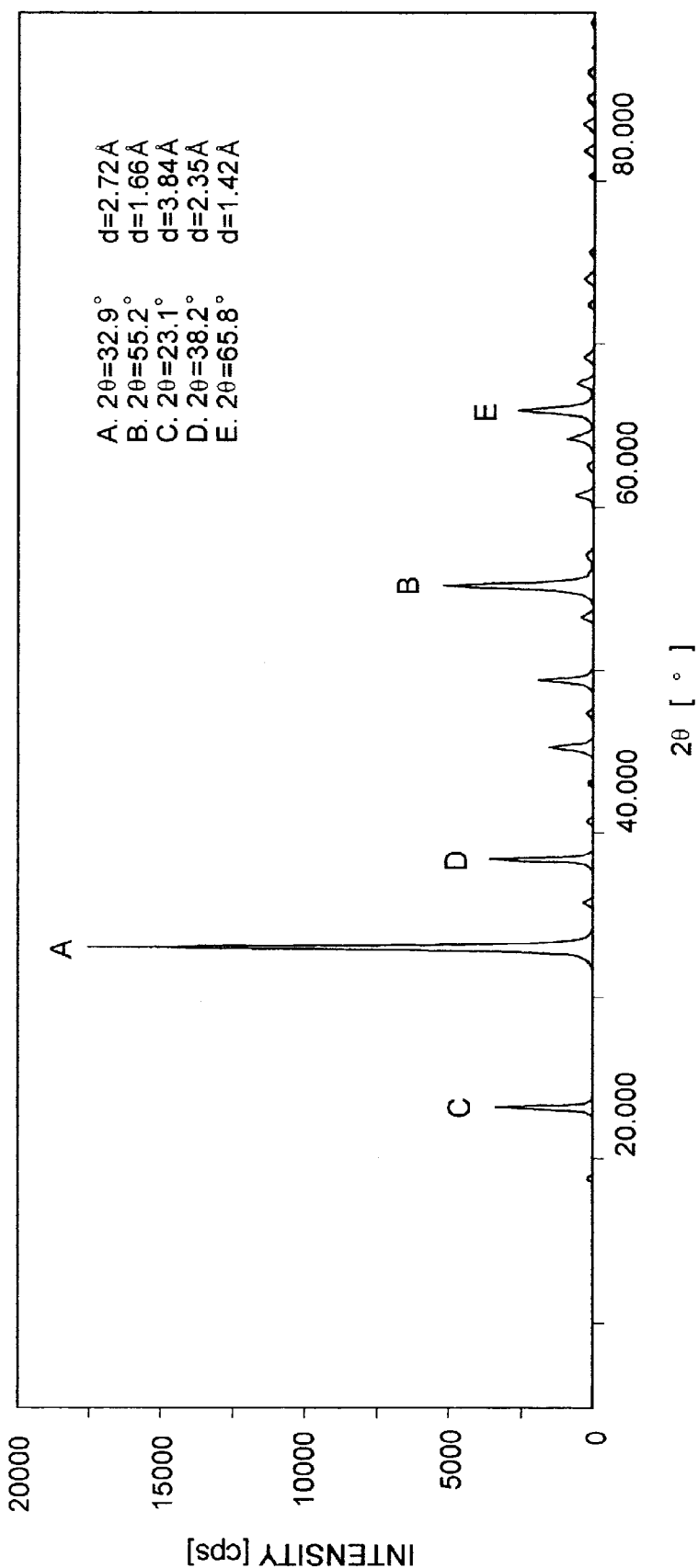

CATALYSTS FOR OXIDATIVE DEHYDROGENATION OF ALKANES AND A PROCESS FOR PRODUCING OLEFINS

TECHNICAL FIELD TO WHICH INVENTION THE INVENTION BELONGS

This invention relates to catalysts for oxidative dehydrogenation of alkanes and a process for producing olefins using said catalysts. More specifically, the invention relates to the catalysts which are suitable for use in vapor phase oxidative dehydrogenation of $C_2$–$C_5$ lower alkanes (hereinafter occasionally referred to simply as "lower alkanes") in the presence of molecular oxygen to produce corresponding olefins, and a process for oxidizing and dehydrogenating lower alkanes at vapor phase with molecular oxygen to produce corresponding olefins at high yields, with the use of said catalysts.

PRIOR ART

Lower olefins are starting materials of important industrial products: Le., ethylene, for ethylene oxide, acetaldehyde, acetic acid and the like; propylene, for acrolein, acrylic acid, propylene oxide, polypropylene and the like; and isobutene, for methacrolein, methacrylic acid, methyl tert.-butyl ether and the like. Demands for those products invariably increasing recently and their prices running higher, development of low cost production process of these lower olefins is desired.

As a production process for lower olefins, in particular, propylene and isobutene, simple dehydrogenation process of lower alkanes is recently reduced to industrial practice. However, this process is subject to an essential problem that it is incapable of giving high conversion due to the equilibrium limitation and furthermore requires high temperatures. Still in addition, deterioration of the catalyst within a short period is inavoidable in said process, which necessitates frequent regeneration of the catalyst using a switch converter or the like. In consequence, plant construction costs and utility costs for running the process are high and, depending on the conditions of factory location, it is unprofitable and its industrial application at the present time is restricted.

Whereas, attempts to produce lower olefins from lower alkanes through oxidative dehydrogenation which is free from the limitation by equlibrium have been made since long, and various catalyst systems therefor have been proposed. Among those known, there are Co—Mo oxide catalyst (U.S. Pat. No. 4,131,631), V—Mg oxide catalyst (U.S. Pat. No. 4,777,319), Ni—Mo oxide catalyst (EP 379,433 A1) $CeO_2/CeF_3$ catalyst (CN 1,073,893A), Mg—Mo catalyst [*Neftekhimiya* (1990), 30(2) 207–10], $V_2O_5/Nb_2O_5$ catalyst [*J. Chem. Commun.* (1991) (8) 558–9], rare earth vanadates catalyst [*Catal. Lett.* (1996), 37, (3,4), 241–6] and $B_2O_3/Al_2O_3$ catalyst [*ACS Symp. Ser.* (1996), 638 (Heterogeneous Hydrocarbon Oxidation) 155–169). Those known catalysts, however, invariably show very low level oxidative dehydrogenation performance and are far short of industrially practicable level.

We also have disclosed for the purpose catalyst containing Cr or Mo, Sb and W as the essential components (2000-037624A-JP) and those containing Mn as the essential component (2000-037625A-JP), but catalysts exhibiting still higher activity level are desirable for industrial use.

THE PROBLEM TO BE SOLVED BY THE INVENTION

An object of this invention is to provide novel oxidative dehydrogenation catalysts useful for vapor phase oxidative dehydrogenation of lower alkanes with molecular oxygen to produce corresponding lower olefins at high yields; and also to provide a process for producing from lower alkanes the corresponding olefins at high yields, by the use of said catalysts.

MEANS FOR SOLVING THE PROBLEM

The above object of the invention can be accomplished by the catalysts which are characterized in that they contain Mn as the essential component and a crystal phase which is identified by the peaks appearing in X-ray diffraction spectrum (per Cu—Kα cathode) when diffraction angle 2θ (±0.3°) is at 32.9°, 55.2°, 23.1°, 38.2° and 65.8° (i.e., when the inherent crystal lattice spacing, d-values, are 2.72 Å, 1.66 Å, 3.84 Å, 2.35 Å and 1.42 Å), that is, the crystal phase corresponding to $Mn_2O_3$. Use of the catalysts in the occasions of vapor-phase oxidative dehydrogenation of $C_2$–$C_5$ lower alkanes enables production of lower olefins at high yields.

EMBODIMENTS OF THE INVENTION

More specifically, in the invention said $C_2$–$C_5$ lower alkanes signify ethane, propane, n-butane, isobutane, n-pentane and isopentane. These lower alkanes may be used either singly or as a mixture of more than one kind.

According to the invention, from these lower alkanes the corresponding olefins can be prepared at high yields, more specifically, ethylene from ethane, propylene from propane, n-butene from n-butane, isobutene from isobutane, n-pentene from n-pentane, and isopentene from isopentane. The invention is particularly suitable for producing propylene from propane and isobutene from isobutane.

The catalysts according to the invention are characterized by containing Mn and a crystal phase identified by the peaks appearing in X-ray diffraction spectrum (per Cu—Kα cathode) when the diffraction angle 2θ (±0.3°) is at 32.9°, 55.2°, 23.1°, 38.2° and 65.8°. In particular, those composed substantially of the elementary composition expressed by the following formula (1) are preferred:

$$Mn_aX_bY_cO_x \qquad (1)$$

in which Mn stands for manganese,

X stands for at least one element selected from the group consisting of Sb, W and Cr, Y stands for at least one element selected from Re, Fe, Co, Ni, Nb, Ta, Ce, Zn, Tl, Li, Na, K, Rb, Cs, Mg, Ca, Sr and Ba, and O stands for oxygen.

Of the catalysts represented by above general formula (1), those containing as the X component at least two elements selected from Sb, W and Cr, or all of those three elements are preferred. Among the preferred catalyst, those containing as the Y component one to four elements selected from the group consisting of Ni, Co, Nb, Ta, Ce, Li, Na and K are particularly advantageous.

Referring to the above general formula (1), a, b, c and x stand for the atomic ratios of Mn, X, Y and oxygen, respectively, and where when a is 1, b is 0.01–2, c is 0–2 and x is a numerical value determined by the extents of oxidation of those elements other than oxygen. Particularly recommendable catalysts are those in which, where a is 1, b is 0.05–1 and c is 0–1.

The oxidative dehydrogenation catalysts of the present invention may further contain refractory inorganic substances for the purpose of improving their activity level and physical durability. Suitable content of the refractory inorganic substances is 10–90% by weight of the whole catalyst containing the catalytically active ingredients. As such refractory inorganic substances, those known can be used, examples of which including silica, alumina, titania, zirconia, silica-alumina, silica-titania and silica-zirconia. In particular, silica, silica-alumina and titania are preferred, because they give higher yield of the object products. As the silica-alumina, those in which the ratio of the silica is at least 10% by weight but less than 100% by weight are suitably used.

The process for preparing the catalysts of the invention are not subject to critical limitations, so long as the catalysts containing the specified crystal phase are ultimately obtained. Whereas, depending on the kind of manganese source used, for example, combination of the preparation steps may become subject to certain limitations such as a need to modify the heat treatment conditions in the subsequent steps. Individual steps, however, are subject to no specific limitation but known methods can be applied. For example, the catalysts according to the invention can be prepared by the following steps: add at least one of antimony trioxide powder, aqueous solution of ammonium metatungstate and aqueous solution of chromium nitrate, to a slurry containing manganese (III) oxide powder; if necessary also add an aqueous solution or an oxide powder of a compound of at least one element selected from the group consisting of Ni, Co, Li, Na, K, Re, Fe, Nb, Ta, Ce, Zn, Tl, Rb, Cs, Mg, Ca, Sr and Ba; optionally further add a refractory inorganic substance such as silica, alumina or the like; stir and mix the resulting slurry for a prescribed period, heat and condense the system; dry the resulting paste at 80–300° C.; grind down and shape the dried system; if necessary crush the shaped pieces to adjust their sizes; and re-dry them at 80–300° C. or if necessary further fire them at 300–800° C.

The above drying and firing may be performed in any kind of atmosphere, such as under high oxygen concentration, low oxygen concentration, in reducing atmosphere, inert gas (nitrogen, helium, argon and the like), or in vacuum. The catalysts of the invention may be contacted with the reaction gases containing alkanes and oxygen, after the drying at temperatures not higher than 300° C., e.g., aforesaid range of 80–300° C., without the high temperature firing such as the one at 300–800° C. as above. In that occasion, the reaction may be initiated directly at a prescribed reaction temperature, or a reaction concurrently serving as a preliminary reaction may be carried out at a temperature higher than the prescribed reaction temperature. In that case, the catalyst's activity variation may be observed during the initial stage of the reaction but it normally stabilizes within an hour. Compared to the case of high temperature firing the catalyst at temperatures not lower than 300° C., e.g., at 300–800° C., in an atmosphere other than the reaction gas, such direct treatment with the reaction gas as above tends to achieve improved activity and selectivity and, therefore, is especially preferred.

Starting materials to be used for the catalyst preparation are not critical, but any of nitrate, sulfate, oxide, hydroxide, chloride, carbonate, acetate, oxygen acid, ammonium salt of oxygen acid, etc. of each metal may be used.

As the Mn source, besides powders of various oxides thereof or molded products which are useful as they are, all of those which can be prepared by generally accepted means, such as manganese hydroxide slurries obtained upon treating an aqueous solution of, e.g., manganese nitrate, with aqueous ammonia or the like, coprecipitation products from aqueous solutions containing manganese compounds and compounds of other catalytically active elements, are useful. Of those, the starting materials containing $Mn_2O_3$, inter alia, manganese oxide composed substantially of $Mn_2O_3$ alone, are preferred. The X-ray diffraction spectrum of such a manganese oxide shows only the peaks identifying the crystal phase corresponding to $Mn_2O_3$.

An ultimately obtained catalyst must contain the crystal phase which is identified by the peaks appearing in its X-ray diffraction spectrum (per Cu—Kα cathode), where the diffraction angle 2θ (±0.3°) is at 32.9°, 55.2°, 23.1°, 38.2° and 65.8°. (i.e., when d-values are 2.72 Å, 1.66 Å, 3.84 Å, 2.35 Å and 1.42 Å) (i.e., the crystal phase corresponding to $Mn_2O_3$). This can be accomplished by either using $Mn_2O_3$ as the Mn source and adopting such preparation conditions as will finally maintain the $Mn_2O_3$ phase, or by adopting such preparation conditions under which $Mn_2O_3$ phase will be formed during the preparation procedure, where the starting material does not contain $Mn_2O_3$. Preferred practice is to use $Mn_2O_3$ as the starting material and not to conduct a heat treatment at temperatures not lower than 300° C.

When Mn oxide is used as the starting material, preferred specific surface area of said material ranges 0.5–10 $m^2/g$. When the area exceeds this range, complete oxidation activity of resulting catalyst becomes intense and high partial selectivity cannot be obtained. Whereas, when the area is less than said range, catalytic activity is reduced.

As the Sb source, powders of oxides such as $Sb_2O_3$, $Sb_2O_4$, $Sb_2O_5$ and the like, Sb oxides as dissolved in aqueous tartaric acid, antimonic acid (antimony pentoxide hydrate) sol, and the like are conveniently used. Of those, antimonic acid sol or $Sb_2O_3$ powder are convenient, in respect of uniform catalyst preparation and performance of resulting catalyst. While antimonic acid sol is commercially available as various products, most of them are unsuitable as starting material for the catalyst because various stabilizers are incorporated therein. An antimonic acid sol which is obtained by passing an aqueous solution of potassium antimonate through a strongly acidic cation exchange resin for effecting ion-exchange is preferred because it is free of impurities.

As starting materials of other elements, use of water-soluble materials is generally preferred, while water-insoluble starting materials such as oxides may also be used depending on kind of the elements.

Form of use of those refractory inorganic substances is not subject to particular limitation, but it can be suitably selected from various forms such as shaped bodies, powder, gel and Sol, according to the individual use form of the catalyst.

The starting gas to be subjected to the vapor phase oxidative dehydrogenation reaction according to the present invention may, if necessary, contain a diluent gas, besides lower alkane(s) and molecular oxygen. As the source of molecular oxygen, air or pure oxygen is used. As the diluent gas, an inert gas such as nitrogen, helium or carbon dioxide, or steam is conveniently used. It is normally satisfactory to use 0.1–5 mols of molecular oxygen per mol of alkane.

The reaction conditions for carrying out the vapor phase oxidative dehydrogenation of the present invention are subject to no critical limitation. For example, the starting gas as described above is contacted with an oxidative dehydrogenation catalyst of the present invention under such conditions as: at a space velocity of 300–30,000 $hr^{-1}$ at a temperature between 250 and 650° C.

While the reaction is normally conducted under atmospheric pressure, a reduced or elevated pressure may be used. Form of the reaction system again is not critical, which may be a fixed bed system, moving bed system or fluidized bed system. It may also be one-pass system or recycling system.

EXAMPLES

Hereinafter the invention is explained in further details referring to working examples, in which conversion, one-pass yield and selectivity are as defined in the following:

$$\text{conversion (mol \%)} = \frac{\text{(mol number of reacted alkane)}}{\text{(mol number of fed alkane)}} \times 100$$

$$\text{selectivity (mol \%)} = \frac{\text{(mol number of each of formed compounds)}}{\text{(mol number of reacted alkane)}} \times 100$$

$$\text{one-pass yield (mol \%)} = \frac{\text{(mol number of each of formed compounds)}}{\text{(mol number of fed alkane)}} \times 100$$

FIG. 1 shows the X-ray diffraction spectrum (per Cu—Kα cathode) of the manganese (III) oxide powder which was used as the Mn source in all of the working examples, in which the horizontal axis indicates the diffraction angle 2θ and the vertical axis, peak intensity (cps).

The main five peaks A, B, C, D and E and all other small peaks invariably are attributable to $Mn_2O_3$ phase.

Figure 2:
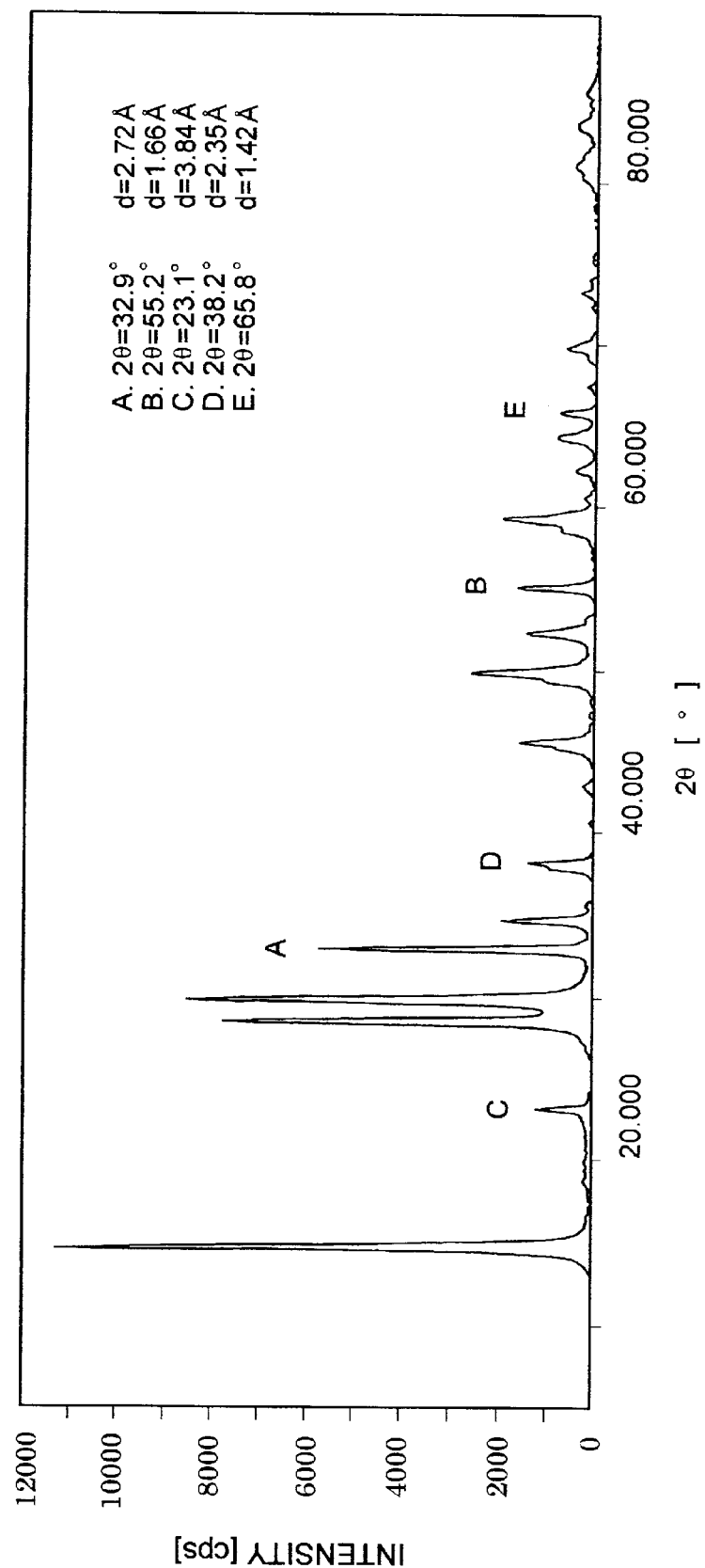

FIG. 2 shows the X-ray diffraction spectrum (per Cu—Kα cathode) of the catalyst which was obtained in Example 1. The horizontal and vertical axes represent the diffraction angle 2θ and the peak intensity, respectively, same as those in FIG. 1.

A, B, C, D and E are attributable to the main five peaks of $Mn_2O_3$ phase. Those peaks appearing when 2θ is at 14.8°, 29.9° and 28.6° are attributable to $H_{14}Sb_{14}O_{21}(OH)_{42}$.

Figure 3:
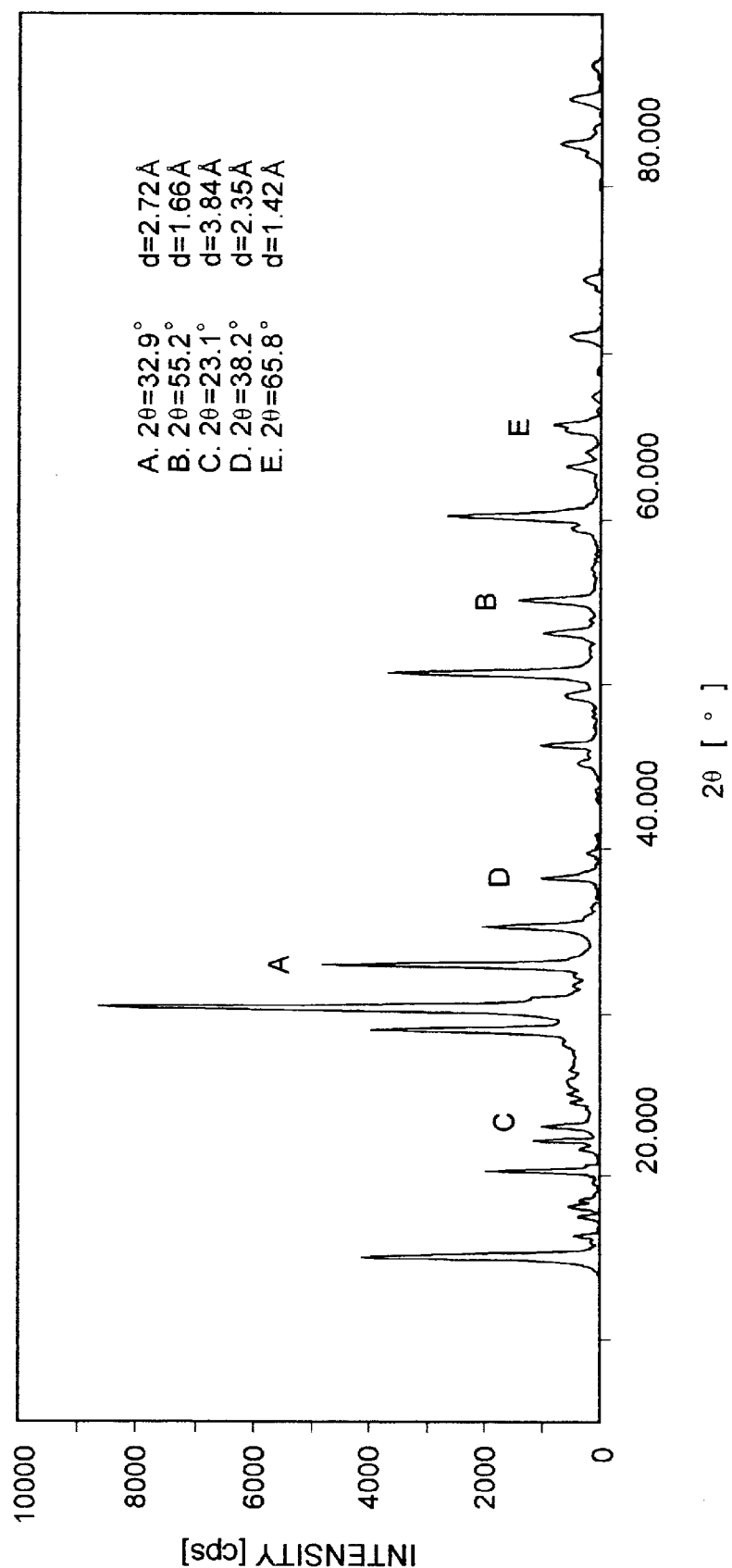

FIG. 3 is the X-ray diffraction spectrum (per Cu—Kα cathode) of the catalyst obtained in Example 16, in which the horizontal and vertical axes represent the same as in FIG. 1.

A, B, C, D and E are attributable to the main five peaks of $Mn_2O_3$ phase.

The peaks appearing when 2θ is at 15.2°, 30.6° and 29.3° are attributable to $Sb_2O_5 \cdot 4H_2O$.

Figure 4:
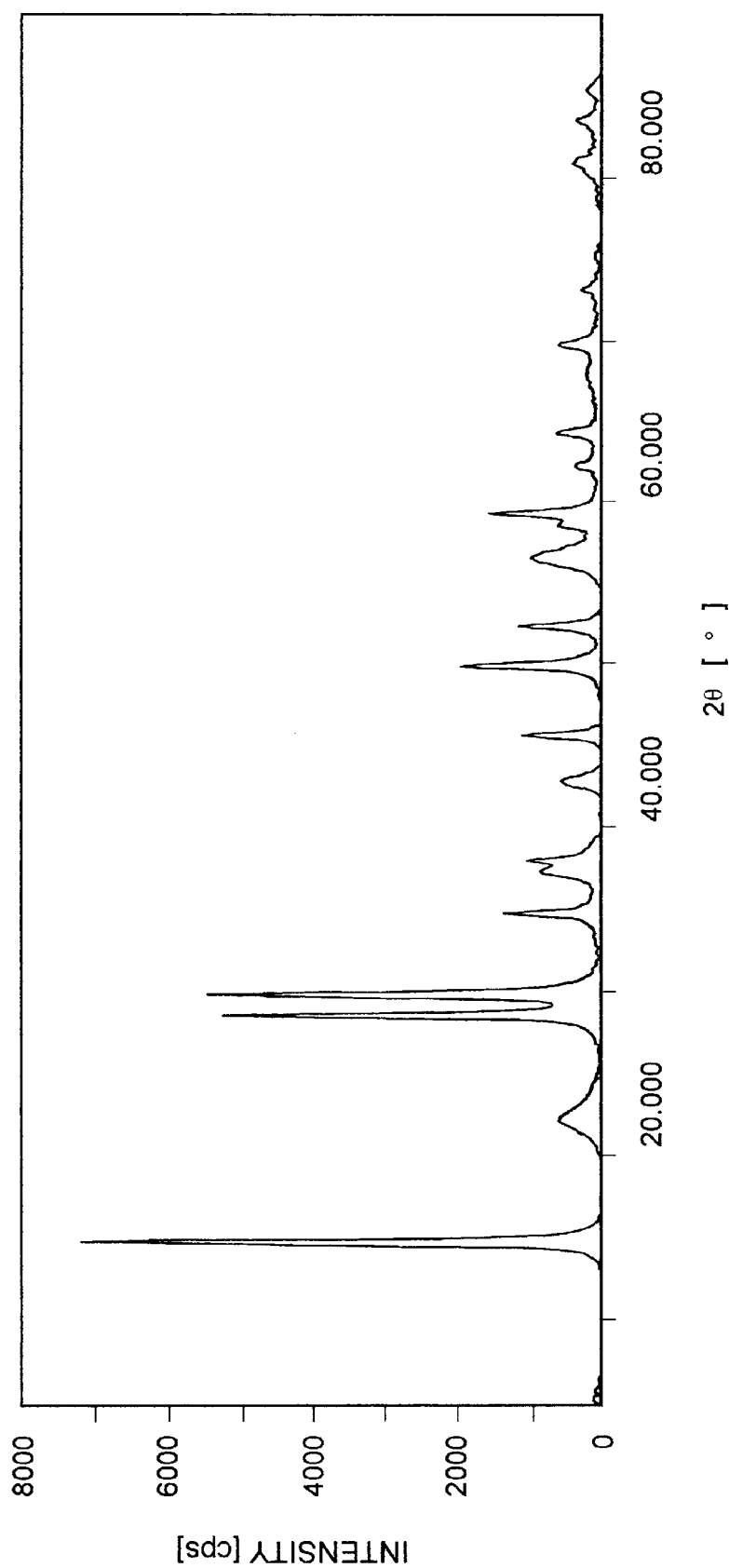

FIG. 4 is the X-ray diffraction spectrum (per Cu—Kα cathode) of the catalyst obtained in Comparative Example 1, in which the horizontal and vertical axes represent the same as in FIG. 1.

There is no peak attributable to $Mn_2O_3$ phase, but the peaks attributable to $MnO_2$ phase appear where 2θ is at 21.8°, 35.1°, 36.8°, 55.3° and 38.4°; and peaks attributable to $H_{14}Sb_{14}O_{21}(OH)_{42}$ appear where 2θ is 14.8°, 29.9° and 28.6°.

Example 1

A manganese (III) oxide powder to be used as the Mn source was prepared as follows.

One hundred (100) g of manganese (IV) dioxide powder (specific surface area=41 m²/g) was put in a crucible and fired in a muffle furnace under ambient pressure at 600° C. for 3 hours. The X-ray diffraction (per Cu—Kα cathode) of the resulting powder was measured, and on the diffraction spectrum the main peaks signifying the presence of the crystal phase corresponding to $Mn_2O_3$ were confirmed where the diffraction angle 2θ (±0.3°) was at 32.9°, 55.2°, 23.1°, 38.2° and 65.8° (i.e., where the d-values were 2.72 Å, 1.66 Å, 3.84 Å, 2.35 Å and 1.42 Å). No other crystal phase was confirmed (FIG. 1). The specific surface area of the manganese (III) oxide powder was 5.0 m²/g.

An antimonic acid sol to serve as the Sb source was prepared as follows: 43.8 g of potassium hexahydroxoantimonate was dissolved in 2 liters of water under heating, and insoluble matter was removed by filtration. The filtrate was passed through a column filled with 500 g of a strongly acidic, cation exchange resin (DOWEX™ 50W×4), at a flow rate of 15 ml/min. to effect an ion-exchange treatment. The resulting liquid was nearly transparent, but after a day, turned to a moderately opaque sol. The Sb concentration in said sol as determined by ICP emission spectrometer was 0.067 mmol/g. The ion-exchange rate was 99.5% and the amount of the residual K in the sol was negligible.

Into a 500-ml beaker, 3.95 g of above manganese (III) oxide powder and 223.9 g of the antimonic acid sol were fed and their agitation under heating was started. After the temperature of the system reached about 80° C., stirring was continued for further 2 hours while maintaining the same liquid level. Stirring was still continued for about 4 hours at 90° C., allowing the system to condense under evaporation of water content. Thus obtained paste was dried at 120° C. for 14 hours, ground down, shaped and crushed to uniformize the size of the granules to 9–20 mesh.

Thus obtained catalyst had a composition of $Mn_1Sb_{0.3}O_x$. In the X-ray diffraction spectrum (per Cu—Kα cathode) of this catalyst, main peaks attributable to $Mn_2O_3$ phase were observed where the diffraction angle 2θ (±0.3°) was at 32.9°, 55.2°, 23.1°, 38.2° and 65.8°. Other than said main peaks, only those peaks of the crystal phase attributable to $H_{14}Sb_{14}O_{21}(OH)_{42}$ were observed (FIG. 2).

This catalyst was charged in an ordinary flow type reactor. The reaction was conducted under the following conditions: The result of the reaction after an hour of initiating the reaction is shown in Table 1.

Amount of the catalyst: 1.5 g
Reaction gas: $C_3H_8/O_2/N_2$=1/1/18 (molar ratio)
Feed rate of the reaction gas:
    112.5 ml (standard condition)/min
Reaction temperature: 490° C.

In the subsequent Examples, the reaction was performed under similar conditions, except in some of them the reaction temperature was varied. The composition of each of the catalyst formed in those Examples and the result of the reaction after an hour of initiating the reaction in each Example are shown in Table 1.

Examples 2 and 3

Catalysts were prepared in the identical manner with Example 1, except that the amount of the antimonic acid sol was changed to 373.2 g and 74.6 g, respectively.

Examples 4 and 5

Catalysts were prepared in the identical manner with Example 1, except that the antimonic acid sol was replaced with an aqueous solution formed by diluting 2.32 g of an aqueous solution of ammonium metatungstate (containing 50% by weight of $WO_3$) with 200 ml of water, or with an aqueous solution formed by dissolving 1.11 g of chromium sulfate tetrahydrate in 200 ml of water under heating, respectively.

Example 6

A catalyst was prepared in the identical manner with Example 1, except that an aqueous solution formed by dissolving 4.00 g of chromium nitrate nonahydrate in 50 ml of water was added to the system after addition of the antimonic acid sol.

Example 7

A catalyst was prepared in the identical manner with Example 6, except that an aqueous solution formed by diluting 2.32 g of an aqueous solution of ammonium metatungstate with 50 ml of water was added instead of the antimonic acid sol.

Example 8

A catalyst was prepared in the identical manner with Example 1, except that the addition of the antimonic acid sol was followed by addition of 2.32 g of an aqueous solution of ammonium metatungstate as diluted with 50 ml of water, and an aqueous solution of 4.00 g of chromium nitrate nonahydrate in 50 ml of water.

Example 9

A catalyst was prepared in the identical manner with Example 8, except that the antimonic acid sol was replaced with 2.19 g of antimony trioxide powder, and the aqueous chromium nitrate solution was replaced with 2.22 g of chromium sulfate tetrahydrate as dissolved in 200 ml of water.

Examples 10–13

Catalysts were prepared in the identical manner with Example 8, except that each of an aqueous solution of 2.91 g of nickel nitrate nonahydrate in 50 ml of water (Example 10), an aqueous solution of 2.92 g of cobalt nitrate nonahydrate in 50 ml of water (Example 11), 5 ml of aqueous potassium hydroxide solution at 0.1 mol/L concentration (Example 12) or 2.5 ml of aqueous lithium hydroxide solution at 0.4 mol/L concentration (Example 13) was added, respectively.

Example 14

A catalyst was prepared in the identical manner with Example 8, except that further 2.5 ml of aqueous lithium hydroxide solution at 0.4 mol/L concentration and 5 ml of aqueous potassium hydroxide solution at 0.1 mol/L concentration were added.

Example 15

A catalyst was prepared in the identical manner with Example 14, except that further an aqueous solution of 2.91 g of nickel nitrate nonahydrate in 50 ml of water was added.

Example 16

A catalyst was prepared in the identical manner with Example 15, except that the aqueous chromium nitrate solution was replaced with an aqueous solution of 1.28 g of chromium sulfate tetrahydrate in 50 ml of water.

Example 17

A catalyst was prepared in the identical manner with Example 16, except that the antimonic acid sol was replaced with 2.19 g of antimony trioxide powder and 200 ml of water.

Example 18

A catalyst was prepared in the identical manner with Example 17, except that the added amount of the aqueous solution of potassium hydroxide at 0.1 mol/L concentration was changed to 12.5 ml.

Examples 19, 20 and 21

Catalysts were prepared in the identical manner with Example 18, except that 1.00 g of niobium pentoxide ($Nb_2O_5$) powder (Example 19), 1.66 g of tantalum oxide ($Ta_2O_5$) powder (Example 20) or 1.29 g of cerium oxide ($CeO_2$) powder (Example 21), respectively, was additionally used.

All of the catalysts prepared in the foregoing Examples gave X-ray diffraction spectra (per Cu—Kα cathode) taken before their use in the olefin-forming reactions, in which the peaks corresponding to $Mn_2O_3$ phase where the diffraction angle 2θ(±0.3°) was at 32.9°, 55.2°, 23.1°, 38.2° and 65.8° (i.e., when d-values were 2.72 Å, 1.66 Å, 3.84 Å, 2.35 Å and 1.42 Å) were observed. No peak attributable to any phase of other Mn oxide only was observed.

The X-ray diffraction spectrum of the catalyst as obtained in Example 16 is shown as FIG. 3.

Comparative Examples 1–9

Catalysts were prepared in the manner identical with Examples 1, 4, 5, 8, 9, 10, 14, 16 and 19, respectively, except that in all of them the manganese (III) oxide powder was replaced with 4.35 g of manganese (IV) dioxide powder (specific surface area=41 $m^2$/g). All of the resulting catalysts gave X-ray diffraction spectra (per Cu—Kα cathode) taken before their use in the olefin-forming reactions, in which $MnO_2$ phase alone was observed and no $Mn_2O_3$ phase was observed.

The X-ray diffraction spectrum of the catalyst as obtained in Comparative Example 1 is shown in FIG. 4.

Oxidative dehydrogenation reaction of propane was conducted, using the catalysts as obtained in Examples 1–21 and Comparative Examples 1–9, respectively. The reaction temperatures used and the results of the reaction after an hour from the initiation of the reaction in each run are shown in Table 1.

TABLE 1

|   |   | Catalyst Composition (atomic ratios excepting oxygen) | Reaction Temp. (° C.) | Propane Conversion (mol %) | Propylene Selectivity (mol %) | Acrolein Selectivity (mol %) | Propylene One-pass Yield (mol %) |
|---|---|---|---|---|---|---|---|
| Example | 1 | $Mn_1Sb_{0.3}$ | 490 | 29.2 | 33.2 | 1.2 | 9.7 |
|  | 2 | $Mn_1Sb_{0.5}$ | 490 | 28.0 | 30.7 | 1.8 | 8.6 |
|  | 3 | $Mn_1Sb_{0.1}$ | 490 | 30.9 | 30.1 | 0.7 | 9.3 |
|  | 4 | $Mn_1W_{0.1}$ | 530 | 24.2 | 33.0 | 0.2 | 8.0 |
|  | 5 | $Mn_1Cr_{0.1}$ | 530 | 28.6 | 31.8 | 0.2 | 9.1 |
|  | 6 | $Mn_1Sb_{0.3}Cr_{0.2}$ | 530 | 36.2 | 38.4 | 0.3 | 13.9 |
|  | 7 | $Mn_1W_{0.1}Cr_{0.2}$ | 530 | 35.3 | 39.9 | 0.1 | 14.1 |
|  | 8 | $Mn_1Sb_{0.3}W_{0.1}Cr_{0.2}$ | 530 | 40.1 | 42.4 | 0.2 | 17.0 |
|  | 9 | $Mn_1Sb_{0.3}W_{0.1}Cr_{0.2}$ | 530 | 39.8 | 42.2 | 0.7 | 16.8 |
|  | 10 | $Mn_1Sb_{0.3}W_{0.1}Cr_{0.2}Ni_{0.2}$ | 530 | 41.6 | 43.7 | 0.2 | 18.2 |

TABLE 1-continued

|  |  | Catalyst Composition (atomic ratios excepting oxygen) | Reaction Temp. (° C.) | Propane Conversion (mol %) | Propylene Selectivity (mol %) | Acrolein Selectivity (mol %) | Propylene One-pass Yield (mol %) |
|---|---|---|---|---|---|---|---|
|  | 11 | $Mn_1Sb_{0.3}W_{0.1}Cr_{0.2}Co_{0.2}$ | 530 | 41.2 | 43.0 | 0.3 | 17.7 |
|  | 12 | $Mn_1Sb_{0.3}W_{0.1}Cr_{0.2}K_{0.01}$ | 530 | 41.8 | 42.8 | 0.6 | 17.9 |
|  | 13 | $Mn_1Sb_{0.3}W_{0.1}Cr_{0.2}Li_{0.02}$ | 530 | 41.9 | 43.0 | 0.7 | 18.0 |
|  | 14 | $Mn_1Sb_{0.3}W_{0.1}Cr_{0.2}Li_{0.02}K_{0.01}$ | 530 | 42.9 | 45.0 | 0.6 | 19.3 |
|  | 15 | $Mn_1Sb_{0.3}W_{0.1}Cr_{0.2}Ni_{0.2}Li_{0.02}K_{0.01}$ | 530 | 42.1 | 48.1 | 0.4 | 20.3 |
|  | 16 | $Mn_1Sb_{0.3}W_{0.1}Cr_{0.2}Ni_{0.2}Li_{0.02}K_{0.01}$ | 530 | 44.3 | 47.4 | 0.3 | 21.0 |
|  | 17 | $Mn_1Sb_{0.3}W_{0.1}Cr_{0.2}Ni_{0.2}Li_{0.02}K_{0.01}$ | 530 | 41.5 | 48.1 | 1.5 | 20.0 |
|  | 18 | $Mn_1Sb_{0.3}W_{0.1}Cr_{0.2}Ni_{0.2}Li_{0.02}K_{0.05}$ | 530 | 35.1 | 50.7 | 2.0 | 17.8 |
|  | 19 | $Mn_1Sb_{0.3}W_{0.1}Cr_{0.2}Ni_{0.2}Li_{0.02}K_{0.05}Nb_{0.15}$ | 530 | 40.7 | 52.3 | 2.5 | 21.3 |
|  | 20 | $Mn_1Sb_{0.3}W_{0.1}Cr_{0.2}Ni_{0.2}Li_{0.02}K_{0.05}Ta_{0.15}$ | 530 | 39.6 | 51.3 | 2.1 | 20.3 |
|  | 21 | $Mn_1Sb_{0.3}W_{0.1}Cr_{0.2}Ni_{0.2}Li_{0.02}K_{0.05}Ce_{0.15}$ | 530 | 42.1 | 49.4 | 1.4 | 20.8 |
| Comparative Example | 1 | $Mn_1Sb_{0.3}$ | 490 | 26.3 | 28.5 | 0.7 | 7.5 |
|  | 2 | $Mn_1W_{0.1}$ | 530 | 23.5 | 29.3 | 0.2 | 6.9 |
|  | 3 | $Mn_1Cr_{0.1}$ | 530 | 26.1 | 27.6 | 0.2 | 7.2 |
|  | 4 | $Mn_1Sb_{0.3}W_{0.1}Cr_{0.2}$ | 530 | 36.6 | 38.8 | 0.1 | 14.2 |
|  | 5 | $Mn_1Sb_{0.3}W_{0.1}Cr_{0.2}$ | 530 | 36.5 | 38.4 | 0.3 | 14.0 |
|  | 6 | $Mn_1Sb_{0.3}W_{0.1}Cr_{0.2}Ni_{0.2}$ | 530 | 36.9 | 39.0 | 0.2 | 14.4 |
|  | 7 | $Mn_1Sb_{0.3}W_{0.1}Cr_{0.2}Li_{0.02}K_{0.01}$ | 530 | 37.6 | 39.9 | 0.3 | 15.0 |
|  | 8 | $Mn_1Sb_{0.3}W_{0.1}Cr_{0.2}Ni_{0.2}Li_{0.02}K_{0.01}$ | 530 | 38.1 | 41.1 | 0.1 | 15.7 |
|  | 9 | $Mn_{1.5}Sb_{0.3}W_{0.1}Cr_{0.2}Ni_{0.2}Li_{0.02}K_{0.05}Nb_{0.15}$ | 530 | 36.5 | 41.8 | 0.1 | 15.3 |

Example 22

The oxidative dehydrogenation reaction as conducted in the identical manner with Example 16, except that isobutane was used in place of propane and the reaction temperature was changed from 530° C. to 490° C. The results of the reaction after an hour from the initiation of the reaction were: isobutane conversion was 35.7 mol %; isobutene selectivity was 32.5 mol %; methacrolein selectivity was 1.0 mol %; and isobutene one-pass yield was 11.6 mol %.

Comparative Example 10

The oxidative dehydrogenation reaction of isobutane was conducted in the identical manner with Example 22, except that the catalyst as obtained in Comparative Example 8 was used. The results of the reaction after an hour from the initiation of the reaction were: isobutane conversion was 28.3 mol %; isobutene selectivity was 27.6 mol %; methacrolein selectivity was 0.8 mol %; and isobutene one-pass yield was 7.8 mol %.

What is claimed is:

1. A process for preparation of olefins, which is characterized in that a catalyst having Mn and a crystal phase identified by the peaks appearing on their X-ray diffraction spectra (per Cu—Kα cathode) where the diffraction angle 2θ (+0.3°) is at 32.9°, 55.20, 23.1°, 38.2° and 65.8° is used in the occasion of oxidizing and dehydrogenating $C_2$–$C_5$ lower alkanes at vapor phase in the presence of molecular oxygen to produce corresponding olefins.

2. A process for preparation of olefins, which is characterized in that a catalyst having Mn and a crystal phase identified by the peaks appearing on their X-ray diffraction spectra (per Cu—Kα cathode) where the diffraction angle 2θ (+0.3°) is at 32.9°, 55.2°, 23.1°, 38.2° and 65.8°, and which is substantially composed of the elementary composition expressed by the following general formula (1):

$$Mn_aX_bY_cO_x \qquad (1)$$

(in which Mn stands for manganese, O stands for oxygen, X stands for at least an element selected from the group consisting of Sb, W and Cr; Y stands for at least an element selected from the group consisting of Re, Fe, Co, Ni, Nb, Ta, Ce, Zn, Tl, Li, Na, K, Rb, Cs, Mg, Ca, Sr and Ba; and a, b, c and x each shows the atomic number of Mn, X, Y and oxygen, respectively, where a is 1, b is 0.01–2, c is 0–2, and x is a numerical value determined by the state of oxidation of the elements other than the oxygen)

is used in the occasion of oxidizing and dehydrogenating $C_2$–$C_5$ lower alkanes at vapor phase in the presence of molecular oxygen to produce corresponding olefins.

* * * * *